(12) United States Patent
Miyata et al.

(10) Patent No.: US 8,021,616 B2
(45) Date of Patent: Sep. 20, 2011

(54) GAS SENSOR

(75) Inventors: Daisuke Miyata, Nishikasugai-gun (JP);
Makoto Hirasawa, Kasugai (JP);
Yoshiaki Matsubara, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 414 days.

(21) Appl. No.: 12/392,361

(22) Filed: Feb. 25, 2009

(65) Prior Publication Data
US 2009/0214389 A1 Aug. 27, 2009

(30) Foreign Application Priority Data

Feb. 25, 2008 (JP) ................................. 2008-042562

(51) Int. Cl.
*G01N 27/12* (2006.01)
*G01N 7/00* (2006.01)
(52) U.S. Cl. ................ 422/83; 422/94; 422/95; 422/96; 422/97; 422/98; 73/1.02; 73/23.31; 73/31.05; 204/424; 204/426; 29/592.1
(58) Field of Classification Search .................... 422/83, 422/94, 95, 96, 97, 98; 73/1.02, 23.31, 31.05; 204/424, 426
See application file for complete search history.

(56) References Cited

U.S. PATENT DOCUMENTS

| | | | | |
|---|---|---|---|---|
| 4,929,414 A * | 5/1990 | Leonard et al. | .................... | 419/2 |
| 5,246,562 A * | 9/1993 | Weyl et al. | ..................... | 204/424 |
| 5,329,806 A * | 7/1994 | McClanahan et al. | ....... | 73/31.05 |
| 5,467,636 A * | 11/1995 | Thompson et al. | .......... | 73/23.31 |
| 5,739,414 A * | 4/1998 | Paulus et al. | ................. | 73/23.31 |
| 5,817,920 A * | 10/1998 | Kuisell et al. | ................ | 73/23.31 |
| 6,082,175 A * | 7/2000 | Yoshikawa et al. | .......... | 73/23.31 |
| 6,266,997 B1 * | 7/2001 | Nelson | .......................... | 73/31.05 |
| 6,347,543 B1 * | 2/2002 | Geier et al. | ................... | 73/23.31 |
| 6,453,726 B1 * | 9/2002 | Gutierrez et al. | ............ | 73/31.05 |
| 6,579,030 B2 * | 6/2003 | Uhler et al. | ................... | 403/348 |
| 6,613,206 B1 * | 9/2003 | Weyl et al. | .................... | 204/424 |
| 6,672,136 B2 * | 1/2004 | Kojima | ........................ | 73/31.05 |

FOREIGN PATENT DOCUMENTS

JP 2006-208165 A 8/2006

\* cited by examiner

*Primary Examiner* — Brian J Sines
(74) *Attorney, Agent, or Firm* — Sughrue Mion, PLLC (57) ABSTRACT

A gas sensor including: a gas detection element; a metal shell extending in an axial direction; and a metal cylinder extending in an axial direction, wherein a leading end portion of the metal cylinder surrounds a base end portion of the metal shell and is fixed to the metal shell via a circumferential welded portion. The metal shell includes: Fe in an amount equal to or more than 50.0 mass %; C in an amount of 0.02 mass % to 0.15 mass %; Cr in an amount of 11.5 mass % to 18.0 mass %; and Nb in an amount equal to or more than twice amount of C in mass %.

7 Claims, 4 Drawing Sheets

GAS SENSOR

BACKGROUND OF THE INVENTION

1. Field of the Invention

This invention relates to a gas sensor, in particular to a gas sensor including a metal shell welded to a metal cylinder, the welded portion having excellent corrosion resistance.

2. Description of the Related Art

A gas sensor provided with a gas detection element configured to change its electrical characteristics depending on concentration of a specific gas component in exhaust gas is used for controlling the air fuel ratio of an automobile. There are various sensors such as an oxygen sensor, an NOx sensor and a HC sensor. The gas sensor includes a gas detection element coaxially inserted into a metal shell. A leading end portion of the gas detection element protrudes from a leading end portion of the metal shell and is exposed to a gas to be measured, such as exhaust gas, so as to detect a specific gas component such as oxygen in the measurement gas.

A sensor output lead wire is connected to a base end portion of the gas detection element protruding from a base end portion of the metal shell via a pair of sensor terminal metal fittings, and a heater lead wire is connected to a ceramic heater inserted into the interior of the gas detection element from a base end side via a pair of heater terminal metal fittings. In order to protect these portions, a metal cylinder is fixed to the base end portion of the metal shell so as to surround their periphery. The metal shell and the metal cylinder are fixed by: fitting a leading end portion of the metal cylinder so as to surround a periphery of the base end portion of the metal shell; and subjecting these portions to circumferential welding. The circumferential welding forms a welded portion in which metal components of the metal cylinder are molten into the metal shell. The welded portion ensures air tightness between the metal shell and the metal cylinder.

The gas sensor is generally used under a severe environment. More specifically, the gas sensor is attached to an exhaust gas pipe of an automobile. Therefore, the gas sensor is heated to a high temperature due to heat from the exhaust gas pipe. Also, the gas sensor is attached to the exhaust gas pipe at a mounting thread portion formed at a leading end side of the metal shell. Consequently, a portion of the gas sensor is exposed to an outside of the exhaust gas pipe. The exposed portion is closer to the base end portion than the mounting thread, which includes a tool engagement portion and the metal cylinder fixed to a base end portion of the metal shell. Therefore, corrosive substances such as a snow melting agent, e.g. calcium chloride or the like, used in cold climate districts easily adheres to the exposed portion.

Since the gas sensor is used under the severe environment described above, the metal shell and the metal cylinder exposed to the outside a r e formed of stainless steel having excellent corrosion resistance. For example, the metal cylinder is formed from SUS304 having excellent corrosion resistance, and the metal shell is formed from SUS430 having cold forgeability although its corrosion resistance is slightly inferior (see JP-A-208165, for example)

SUMMARY OF THE INVENTION

However, when circumferential welding is performed on the metal cylinder and the metal shell, a welded portion is formed in which metal components of the metal cylinder are molten into the metal shell. However, chrome carbonate precipitates in the vicinity of a boundary (closer to the metal shell from the boundary) between the welded portion and the metal shell due to bonding of Cr and C. Accordingly, a Cr-depleted layer having a reduced Cr content is formed around a peripheral portion of the chrome carbonate. Since Cr is an element effective for improving corrosion resistance, the Cr-depleted layer having a reduced Cr content is easily corroded.

When the Cr-depleted layer is formed in the vicinity of the boundary between the welded portion and the metal shell, corrosion may proceed to an entire portion of the boundary between the welded portion and the metal shell along the Cr-depleted layer. As a result, water and corrosive substances may infiltrate the interior of the metal shell from the outside through the corroded portion. Further, the components housed in the metal shell such as the gas detection element and the ceramic heater are damaged by water and corrosive substances which have infiltrated, thereby making accurate measurement of gas concentration difficult.

Particularly, when the metal cylinder includes stainless steel having a chemical composition according to SUS304 having excellent corrosion resistance, and the metal shell includes stainless steel having a chemical composition according to SUS430 that is slightly inferior in corrosion property than SUS304, the formation of a Cr-depleted layer in the vicinity of the boundary becomes prominent, and accelerated corrosion proceeds along the entire portion of the boundary along the Cr-depleted layer.

The present invention was made in consideration of the above circumstances, and an object thereof is to provide a gas sensor which is capable of suppressing corrosion at the welded portion of the metal cylinder and the metal shell, and which is capable of maintaining accurate measurement of gas concentration over a long period of time.

The above object has been achieved, in accordance with a first aspect of the invention, by providing a gas sensor which comprises a gas detection element extending from a leading end thereof to a base end thereof in an axial direction, the leading end of the gas detection element being exposed to a gas to be measured; a metal shell extending from a leading end thereof to a base end thereof in the axial direction and holding the gas detection element such that the gas detection element protrudes from the leading end of the metal shell; and a metal cylinder extending from a leading end thereof to a base end thereof in the axial direction, a leading end portion of the metal cylinder surrounding a base end portion of the metal shell and being fixed to the metal shell via a circumferential welded portion, wherein the metal shell comprises: Fe in an amount equal to or more than 50.0 mass %; C in an amount of 0.02 mass % to 0.15 mass %; Cr in an amount of 11.5 mass % to 18.0 mass %; and Nb in an amount equal to or more than twice the amount of C in mass %.

The metal shell may further comprise Si in an amount of more than 0 mass % but not more than 1.00 mass %; Mn in an amount of more than 0 mass % but not more than 1.25 mass %; P in an amount of more than 0 mass % but not more than 0.06 mass %; and S in an amount of more than 0 mass % but not more than 0.20 mass %.

The metal shell may comprise C in an amount of 0.02 mass % to 0.06 mass %; Si in an amount of more than 0 mass % but not more than 1.00 mass %; Mn in an amount of more than 0 mass % but not more than 1.00 mass %; P in an amount of more than 0 mass % but not more than 0.04 mass %; and S in an amount of more than 0 mass % but not more than 0.03 mass %.

Further, in the gas sensor of this invention, the amount of C contained in the metal cylinder may be smaller than that contained in the metal shell in mass %.

Further, in the gas sensor, the welded portion at an outer surface of the metal shell may have a length in the axial direction of not less than 0.4 mm but not more than 0.7 mm, as viewed in a section on a plane including an axis of the metal shell.

Further, in the gas sensor, a maximum depth of the welded portion defined from the outer surface of the metal shell of the welded portion in a radial direction may be equal to or less than a half of a thickness of the base end portion of the metal shell in the radial direction.

In the gas sensor, the amount of Nb contained in a portion of the metal shell in a vicinity of a boundary with the welded portion may be smaller than the amount of Nb contained in other portions of the metal shell, which are not located in the vicinity of the boundary with the welded portion.

According to the above-described aspect of the invention, in a gas sensor in which a leading end portion of a metal cylinder is fitted to surround a base end portion of a metal shell by circumferential welding, it is possible to suppress corrosion in a welded portion as well as damage to elements housed in the metal shell such as a gas detection element and a ceramic heater. This is achieved by using a metal shell comprising Fe in an amount of 50.0 mass % or more, 0.02 mass % to 0.15 mass % of C, 11.5 mass % to 18.0 mass % of Cr, and Nb in an amount equal to or more than twice that of C in mass %.

Since Nb is present, it is possible to form niobium carbonate by bonding Nb with C before chrome carbonate is formed by bonding between C and Cr in the case of circumferential welding of the metal shell and the metal cylinder. Therefore, it is possible to suppress formation of a chrome-depleted layer by suppressing local reduction of Cr in the vicinity of the boundary between the metal shell and the welded portion in which metal components of the metal cylinder are molten into the metal shell.

It is possible to suppress the progress of corrosion in an entire portion of the boundary between the welded portion and the metal shell by suppressing formation of a chrome-depleted layer in the vicinity of the boundary between the welded portion and the metal shell as described above. As a result, it is possible to suppress infiltration of water and corrosive substances into the interior of the gas sensor as well as damage to the elements housed in the metal shell such as the gas detection element and the ceramic heater, thereby making it possible to perform accurate measurement of gas concentration over a long period of time.

DESCRIPTION OF THE EMBODIMENTS

Hereinafter, each of the components of a metal shell according to an embodiment of the invention will be described in greater detail. However, the present invention should not be construed as being limited thereto.

C is an element effective for promoting strength. The metal shell of the embodiment includes C in an amount of 0.02 mass % to 0.15 mass %, more preferably 0.02 mass % to 0.06 mass %. If the C content of the metal shell is less than 0.02 mass %, it is difficult to ensure the strength of the metal shell. In addition, abnormal growth of crystal grains may occur in a process for producing the metal shell such as a wire drawing process, which may make it difficult to perform a subsequent process such as cold processing. Further, from an industrial point of view, it is not easy to produce a metal shell having a low C content of less than 0.02 mass %. In contrast, if the C content exceeds 0.15 mass %, a chrome-depleted layer tends to form due to bonding between C and Cr when the metal shell is welded to the metal cylinder, and the toughness of the metal shell may thereby be reduced. From the view point of further suppressing formation of the chrome-depleted layer and toughness reduction, the C content is preferably 0.06 mass % or less.

Cr is an element effective for improving corrosion resistance. The metal shell of the embodiment includes Cr in an amount of 11.5 mass % to 18.0 mass %. Cr improves corrosion resistance by enhancing densification of a surface rust coating and environmental shielding that is a property to shield against environment (atmosphere). However, it is difficult to sufficiently ensure corrosion resistance when the Cr content is less than 11.5 mass %. In contrast, if the Cr content exceeds 18.0 mass %, processability in production of the metal shell is deteriorated. Therefore, from the view point of balance between corrosion resistance and productivity, the Cr content is set within a range of from 11.5 mass % to 18.0 mass %.

Nb is added to suppress the formation of a chrome-depleted layer in the vicinity of a surface of the welded portion when welding the metal shell and the metal cylinder as described above. Also, since it is possible to suppress formation of a chrome-depleted layer by adding Nb, it is no longer necessary to excessively reduce the content of C that is involved in forming chrome-depleted layer. Thus, the C content in the metal shell may be set to 0.02 mass % or more as described above.

The content of Nb in the metal shell is equal to or more than twice the content of C in mass %. When the Nb content is less than twice the content of C, it is difficult to sufficiently suppress the formation of a chrome-depleted layer. From the view point of further suppressing the formation of a chrome-depleted layer, the Nb content may preferably be equal to or more than three times the content of C in mass %.

An upper limit of the Nb content is not particularly limited insofar as the Nb content is equal to or more than twice, more preferably three times, the content of C in mass %, but the upper limit may preferably be 60 times the content of C or less. It is possible to satisfactorily suppress generation of the chrome-depleted layer when the content of Nb is about 60 times the content of C in mass %, and an Nb content exceeding 60 times the content of C may undesirably deteriorate processability of the metal shell and increase production cost. The Nb content is more preferably be 30 times the content of C in mass % from the view point of suppressing the generation of a chrome-depleted layer while maintaining processability of the metal shell and avoiding a substantial increase in production cost.

The metal shell of this embodiment contains Fe in an amount of 50.0 mass % or more, and C, Cr and Nb in amounts defined above. The metal shell may also contain one or more selected from Si, Mn, P and S in addition to the above-specified components.

Si is an element effective for deoxidation and promoting strength. However, weldability and the like may deteriorate when the Si content of the metal shell is excessive. Therefore, the Si content in the metal shell is preferably 1.00 mass % or less. From the view point of deoxidation and promoting strength, the Si content of the metal shell is preferably 0.01 mass % or more.

Mn is an element equally effective as Si for deoxidation and promoting strength. However, the toughness of the metal shell may deteriorate when the Mn content of the metal shell is excessive. Therefore, the Mn content in the metal shell is preferably 1.25 mass % or less, more preferably 1.00 mass % or less. From the view point of deoxidation and promoting strength, the Mn content of the metal shell is preferably 0.01 mass % or more.

P is present as an impurity in manufacturing the metal shell, but may be harmful for corrosion resistance and may deteriorate toughness and weldability. Therefore, the P content in the metal shell is preferably kept as small as possible, and the P content is preferably 0.06 mass % or less, more preferably 0.04 mass % or less.

S may be present in the metal shell so as to effectively improve cutting properties. However, since excessive addition of S may deteriorate cold processability, the content of S is preferably 0.20 mass % or less. Further, since S is equally harmful to corrosion resistance as P, the S content is preferably kept as small as possible, and the S content is preferably 0.03 mass % or less.

The metal shell of this embodiment may contain one or more elements selected from Ni, Cu and Mo.

Ni is an element effective for improving corrosion resistance. However, when the Ni content in the metal shell is excessively large, hot processability during production may deteriorate, and productivity of the metal shell may be reduced. Therefore, the Ni content in the metal shell is preferably 0.60 mass % or less.

Cu is also an element effective for improving corrosion resistance. More specifically, Cu improves corrosion resistance by environmental shielding and by enhancing densification of a surface rust coating. However, when the Cu content in the metal shell is excessively large, hot processability during production may deteriorate, and productivity of the metal shell may be reduced. Therefore, the Cu content in the metal shell is preferably 0.60 mass % or less.

Mo is also an element effective for improving corrosion resistance. However, when the Mo content in the metal shell is excessively large, hot processability during production may deteriorate, and productivity of the metal shell may be reduced. Therefore, the Mo content in the metal shell is preferably 0.60 mass % or less.

It is possible to produce the metal shell of this embodiment in the same manner as a metal shell of related-art gas sensors, except for having the above-specified chemical composition. More specifically, the metal shell may be produced by: melting a stainless steel in which a chemical composition is adjusted such that the Nb content thereof is equal to or more than twice, preferably within a range from 5 to 60 times, the content of C based on the chemical composition of SUS430 or SUS430F; performing rolling and wire drawing of the molten stainless steel; and forming the metal shell into a predetermined shape by cold forging.

The individual components of the metal shell may be detected by x-ray fluorescence. Further, the content (amount) of the individual components may be determined by performing chemical analysis optimum for the various components detected by X ray fluorescence.

Figure 1:
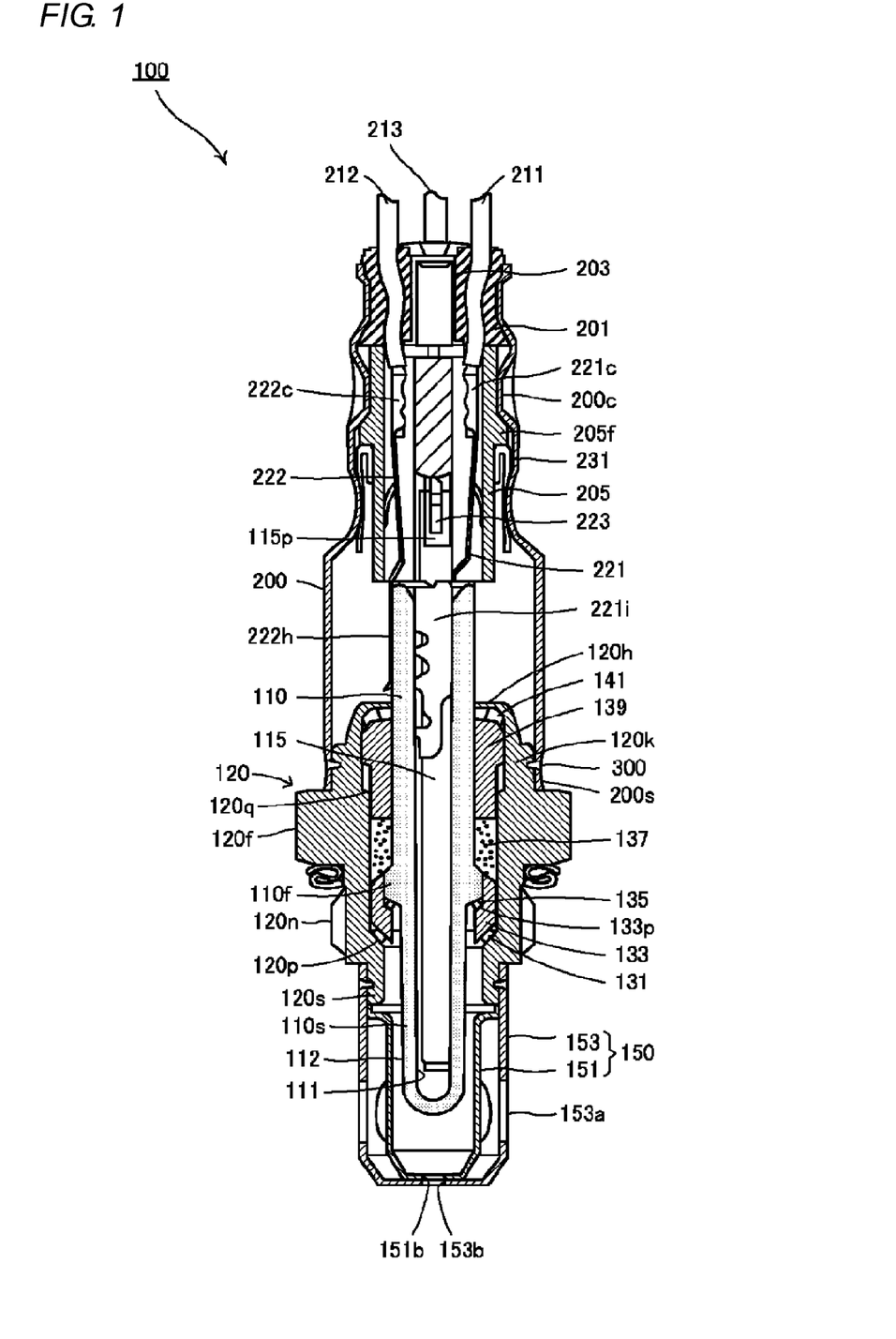
FIG. 1 is a sectional view showing an example of a gas sensor according to an embodiment of the invention.

Hereinafter, a gas sensor according to this embodiment using the metal shell will be described specifically with reference to the drawings. FIG. 1 is a sectional view showing one example of the gas sensor according to an embodiment of the invention. The illustrated example is an oxygen sensor to be attached to an exhaust gas pipe of an internal combustion for detecting oxygen concentration in exhaust gas. In FIG. 1, a leading end portion of the gas sensor is shown in a lower portion, and a base end portion is shown in an upper portion of the drawing.

The gas sensor 100 includes: a gas detection element 110 extending in an axial direction; a cylindrical metal shell 120 surrounding a periphery of the gas detection element 110; a protector 150 covering a leading end portion 110s of the gas detection element 110, the leading end portion 110s being exposed to the exhaust gas; and a metal cylinder 200 covering a base end side of the metal shell 120.

The gas detection element 110 is formed into a bottomed cylindrical shape having a closed leading end portion 110s, and is formed mainly from partially stabilized zirconia obtained by solid dissolution using yttria as a stabilizer. A porous internal electrode layer 111 made from Pt or a Pt alloy is formed to cover an entire portion of an inner periphery of the gas detection element 110, and a similar porous outer electrode layer 112 is formed on an outer periphery thereof.

An engagement flange portion 110f protruding radially outwardly is provided at a substantially middle position of the gas detection element 110 in the axial direction, and the engagement flange portion 110f is used for retaining the gas detection element 110 in the metal shell 120. A ceramic heater 115 having a round bar shape and including a heating resistor provided therein is inserted inside the gas detection element 110.

The metal shell 120 has a chemical composition having an Nb content equal to or more than twice the content of C in mass % as described above. The metal shell 120 has a leading end portion 120s having a small diameter at a leading end side, and the leading end portion 120s is inserted into a protector 150. A rack portion 120p for holding the gas detection element 110 in the axial direction is formed at a position on an inner periphery of the metal shell 120 and closer to the base end side than the leading end portion 120s. Further, a step portion 120q is formed at a position on the inner periphery of the metal shell 120 and closer to the base end side than the rack portion 120p.

A mounting thread portion 120n is formed for mounting the gas sensor 100 to the exhaust gas pipe. The mounting thread portion 120n is formed on the outer periphery of the metal shell 120 and at a position closer to the base end portion than the leading end portion 120s. Further, a hexagonal flange portion 120f used as a tool engagement portion when mounting the gas sensor 100 to the exhaust pipe is formed at a position closer to the base end portion than the mounting thread portion 120n.

The metal shell 120 coaxially retains the gas detection element 110 such that the leading end portion 110s of the gas detection element 110 protrudes from a leading end surface of the metal shell 120. More specifically, a first plate packing 131 is disposed on the rack portion 120p of the metal shell 120, and a cylindrical first fixing member 133 having a step portion 133p on its inner periphery is disposed adjacent to the first packing 131 in a direction of the base end side. The gas detection element 110 is inserted into the first fixing member 133, and the engagement flange portion 110f is engaged with the step portion 133p of the first fixing member 133 via a second plate packing 135. A sealing filler layer 137 obtained by compression filling of talc is disposed in a gap located adjacent to the first fixing member 133 in the base end side direction and defined between the outer periphery of the gas detection element 110 and the inner periphery of the metal shell 120.

A cylindrical second fixing member 139 through which the gas detection element 110 penetrates is disposed adjacent to the sealing filler layer 137 in the base end side direction. A crimping ring 141 is disposed adjacent to the second fixing member 139 in the base end side direction, and a crimping portion 120h of the metal shell 120 is crimped in a radially inward direction so that the gas detection element 110 is air-tightly retained in the metal shell 120.

Figure 2:
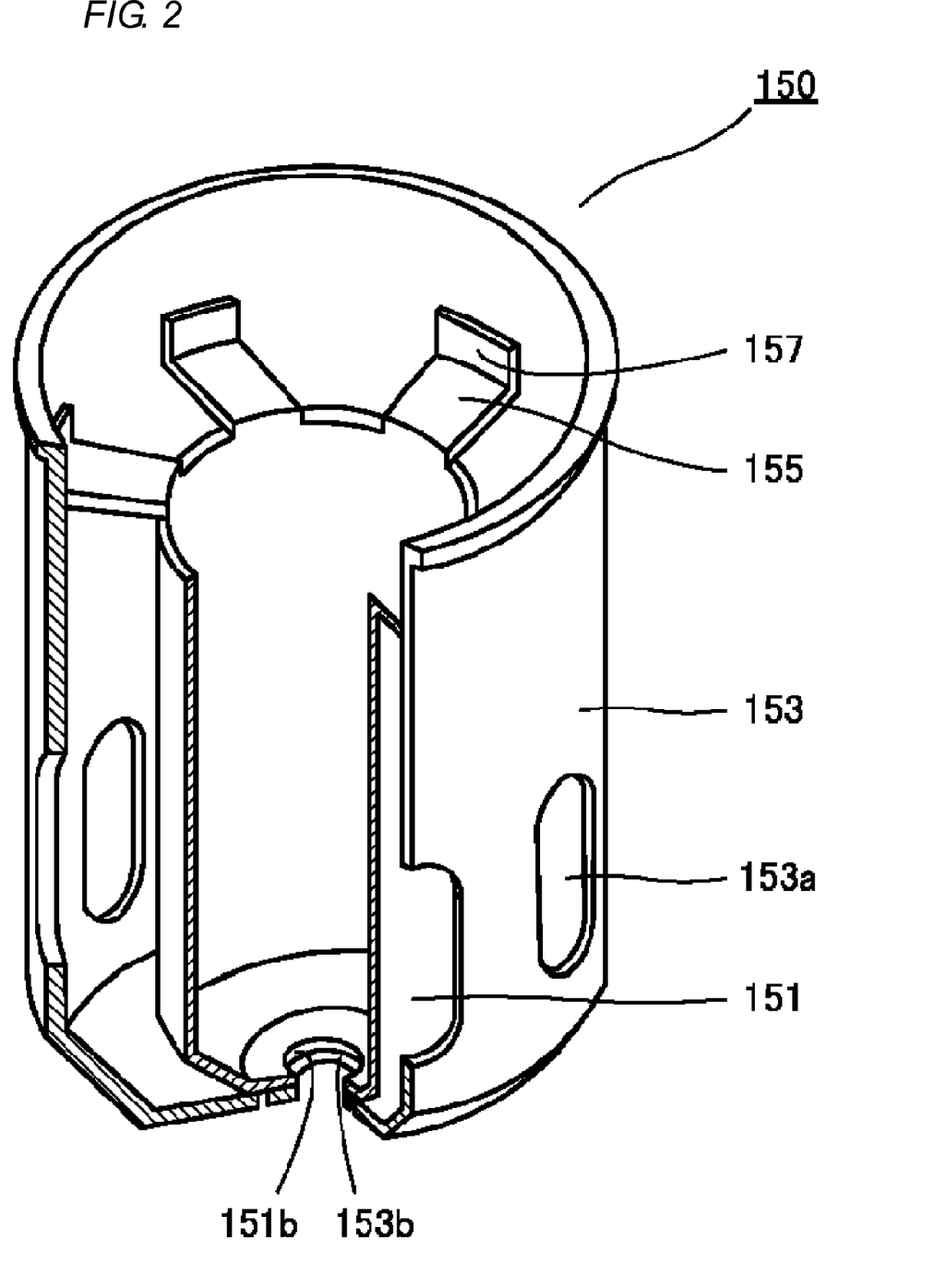
FIG. 2 is an enlarged external view showing a protector of the gas sensor of FIG. 1.

As shown in FIG. 2 illustrating an enlarged view, the protector 150 has a double structure including a cylindrical inner cover portion 151 covering the leading end portion 110s of the gas detection element 110 via a gap and a cylindrical outer cover portion 153 disposed on an outer periphery of the inner cover portion 151.

Outer gas circulation holes 153a allow the exhaust gas to be introduced from the outside to the inside and are provided on a lateral surface portion of the outer cover portion 153. Each of the outer gas circulation holes 153a has an oval shape, and the outer gas circulation holes 153a are formed at constant intervals in a circumferential direction at a position closer to the leading end side from the center as viewed in the axial direction. Also, an outer leading end circulation hole 153b having a circular shape is provided at a leading end portion of the outer cover portion 153. Though the inner cover portion 151 is not provided with any gas circulation hole, an inner leading end circulation hole 151b is formed at the leading end portion of the inner cover portion 151.

The protector includes blocking portions 155 provided in a space defined between the inner cover portion 151 and the outer cover portion 153 and positioned closer to the base end side than the outer gas circulation holes 153a. The blocking portions 155 intermittently block the space in the circumferential direction. Each of the blocking portions 155 is formed by radially outwardly bending a base end side of the inner cover portion 151. A leg portion 157 is provided at a radially outward portion of each of the blocking portions 155 and is bent in the base end side direction. The protector 150 is fixed to the metal shell 120 by laser welding in a state where a base end portion of the outer cover portion 153 is pressed into and fixed at the leading end portion 120s of the metal shell 120.

Referring back to FIG. 1, the metal cylinder 200 is disposed at a base end portion 120k of the metal shell 120 to cover the periphery of the metal shell 120. The metal shell 120 and the metal cylinder 200 are subjected to circumferential laser welding at the base end portion 120k and the leading end portion 200s and fixed by a welded portion 300 in which metal components of the metal cylinder 200 are molten into the metal shell 120. The metal cylinder 200 may preferably have a C content smaller than that of the metal shell 120 and can be formed from SUS304, for example, that has excellent corrosion resistance. The content of C in the welded portion 300 in which the metal shell 120 and the metal cylinder 200 are welded also becomes smaller than that of the metal shell 120 by maintaining the C content of the metal cylinder 200 smaller than that of the metal shell 120. Therefore, a chrome-depleted layer is hardly or never formed from a boundary between the welded portion 300 and the metal shell 120 to the welded portion 300. Consequently, the progress of corrosion to an entire portion of the boundary is suppressed.

Figure 3:
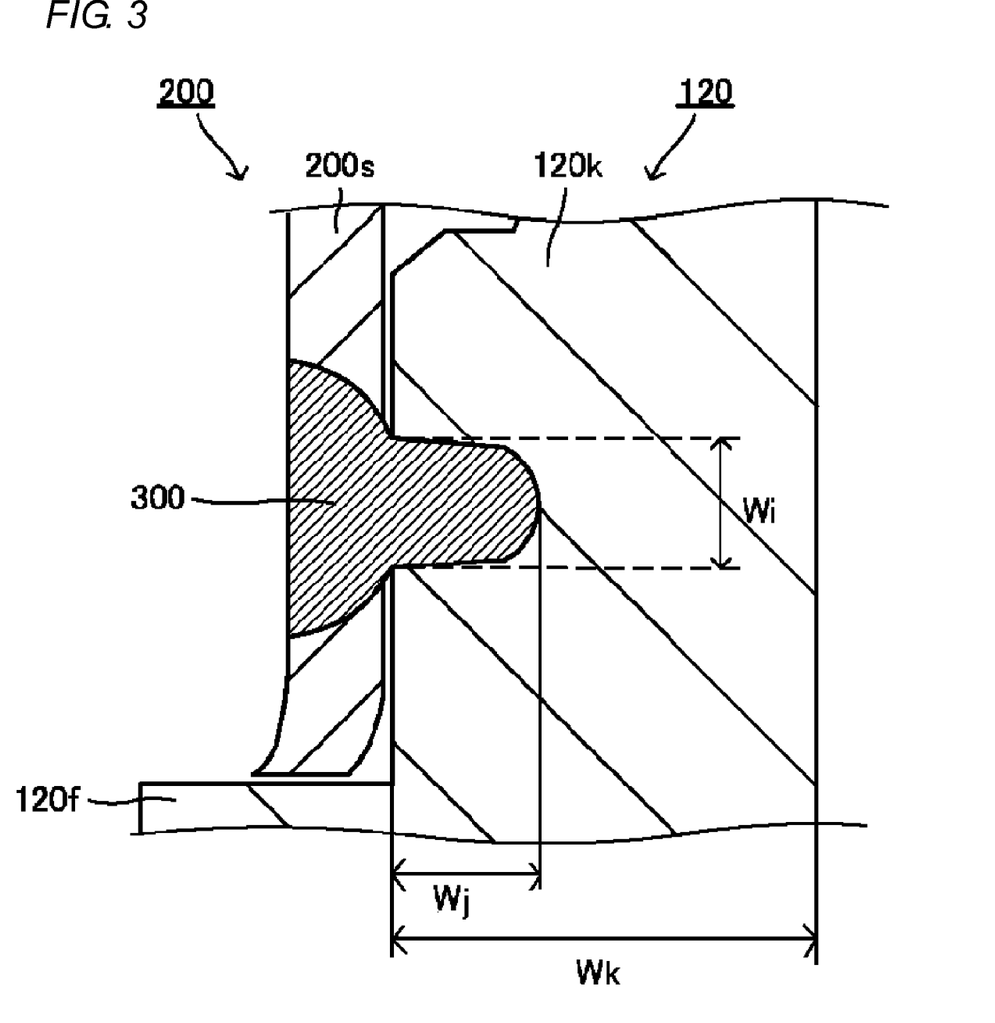
FIG. 3 is an enlarged schematic sectional view showing a welded portion of the gas sensor of FIG. 1.

FIG. 3 is a diagram showing an enlarged view of the welded portion 300 of the metal shell 120 and the metal cylinder 200. The welded portion 300 shown in FIG. 3 corresponds to a left side portion of the welded portion 300 of the gas sensor 100 shown in FIG. 1.

The welded portion 300 is formed such that metal components contained in the metal cylinder 200 are molten into the metal shell 120 as described above. According to this embodiment, since the formation of chrome-depleted layer in the vicinity of the boundary (closer to the metal shell 120 from the boundary) between the welded portion 300 and the metal shell 120 is suppressed by using the above-specified materials for the metal shell 120, the progress of corrosion to the entire portion of the boundary is also suppressed. Specifically, Nb in the metal shell 120 in the vicinity of the boundary with the welded portion 300 reacts with C to form Nb carbide. As a result, the Nb content (mass %) of a portion of the base end portion 120k of the metal shell 120 in a vicinity of the boundary with the welded portion 300 is less than that of other portion of the base end portion 120k (e.g., in a vicinity of an inner surface). That is, an Nb depleted layer is formed which suppresses formation of a chrome-depleted layer. Accordingly, since the progress of corrosion to the entire portion of the boundary is suppressed, water and corrosive substances are completely blocked by the welded portion 300 formed between the metal shell 120 and the metal cylinder 200. This is the case even when water and corrosive substances infiltrate from a narrow gap between a base end surface of the hexagonal flange portion 120f and a leading end surface of the leading end portion 200s, because further infiltration is suppressed. As a result, damage to the gas detection element, the ceramic heater and the like housed inside the metal shell is suppressed to enable accurate measurement of gas concentration over a long period of time.

The size of the welded portion 300 is not particularly limited, but a length thereof in the axial direction (vertical direction in the drawing) of the gas sensor 100, i.e. a length (Wi in the drawing) to an outer surface of the metal shell 120, for example, is preferably 0.4 mm to 0.7 mm (Wi=0.5 mm in this embodiment).

This embodiment exhibits a prominent effect as compared to related art examples when the length Wi of the welded portion 300 is 0.7 mm or less. In other words, when the length Wi of the welded portion 300 is short such as 0.7 mm or less, a length (hereinafter referred to as a boundary length) along the boundary between the welded portion 300 and the metal shell 120 is also shortened to allow corrosion to progress to the entire portion of the boundary. However, in this embodiment, since formation of a chrome-depleted layer is suppressed, the progress of corrosion to the entire portion of the boundary is suppressed even in the case of the above-specified boundary length. As a result, damage to the elements housed in the metal shell 120 such as the gas detection element and the ceramic heater is suppressed to enable accurate measurement of gas concentration over a long period of time. When the length Wi of the welded portion 300 is less than 0.4 mm, adequate welding strength is not obtained in some cases.

Particularly, from a production point of view, a radial maximum depth (Wj in the drawing) from the outer surface of the metal shell becomes equal to or less than a half of the thickness (Wk in the drawing) of the base end portion 120k of the metal shell 120 in some cases. Such depth inevitably shortens the boundary length to shorten the length Wi of the welded portion 300 to 0.7 mm or less in some cases. Even in such a case, the formation of a chrome-depleted layer is suppressed, so that damage to the elements housed in the metal shell, such as the gas detection element and the ceramic heater, is suppressed to enable accurate measurement of gas concentration over a long period of time. In this embodiment, Wj=0.7 mm, and Wk=2.7 mm.

Referring back to FIG. 1, a grommet 201 formed from a fluorine rubber is inserted at the base end side of the metal cylinder 200. The grommet 201 radially outwardly crimps the metal cylinder 200 to be air-tightly fixed to the metal cylinder 200.

A through hole is provided at a central portion of the grommet 201, and a filter member 203 is disposed in the through hole. The filter member 203 introduces air into the inside of the metal cylinder 200 while preventing infiltration of moisture. A separator 205 made from insulating alumina is disposed at a leading end side of the grommet 201. Sensor output lead wires 211 and 212 and a heater lead wire 213 are disposed so as to penetrate through the grommet 201 and the separator 205. Also, connector portions 221c and 222c of first and second sensor terminal metal fittings 221 and 222 and a heater terminal metal fitting 223 that are insulated from one another are disposed inside the separator 205, and a base end side of the ceramic heater 115 is also housed in the separator 205.

The first sensor terminal metal fitting 221 holds and is electrically connected to the sensor output lead wire 211 by crimping the sensor output lead wire 211 to the connector portion 221c. The first sensor terminal metal fitting 221 is also electrically connected to the inner electrode layer 111 by inserting an insertion portion 221i into a bottomed hole of the gas detection element 110. The second sensor terminal metal fitting 222 holds and is electrically connected to the sensor output lead wire 212 by crimping the sensor output lead wire 212 to the connector portion 222c. The second sensor terminal metal fitting 222 is also electrically connected to the outer electrode layer 112 by holding the outer periphery in the vicinity of a base end of the gas detection element 110 at a holding portion 222h.

The two second sensor terminal metal fittings 223 are respectively connected to the heater lead wires 213 (the other heater lead wire is omitted since FIG. 1 is a sectional view) and bonded to a pair of electrode pads 115p of the ceramic heater 115 to be electrically connected to the electrode pads 115p.

A guard portion 205f protruding radially outwardly is formed on the separator 205, and four inner protruding portions 200c are formed on the metal cylinder 200 at a constant interval along the circumferential direction. The separator 205 is retained in the metal cylinder 200 by urging the guard portion 205f to the base end side by means of an urging member 231 in a state where a base end surface of the guard portion 205f abuts the inner protruding portion 200c. The urging member 231 is retained by the separator 205 due to its cylindrical form and elasticity, and is deformed when the metal cylinder 200 adjacent to the urging member 231 in a radially outward direction is crimped in a radially inward direction, thereby urging the guard portion 205f of the separator 205 to the base end side.

Next, a method of producing the gas sensor 100 will be described.

At first, the outer cover portion 153 and the inner cover portion 151 are prepared. Each of the outer cover portion 153 and the inner cover portion 151 has a bottomed cylindrical shape and is made from SUS310S, which have previously been molded into predetermined dimensions. Then, spot welding is performed on four positions around the inner leading end circulation hole 151b and the outer leading end circulation hole 153b. Accordingly, the inner cover portion 151 and the outer cover portion 153 are coaxially fixed to each other, thereby obtaining the protector 150. Meanwhile, plasticity processing and cutting processing are performed on a stainless steel having the above-described chemical composition to obtain the cylindrical metal shell 120.

After fitting the outer cover portion 153 of the protector 150 to the leading end portion 120s of the metal shell 120, laser welding is performed on the outer periphery of the outer cover portion 153. Thus, the protector 150 and the metal shell 120 are firmly fixed to each other by press-fit fixing and laser welding.

To the inside of the metal shell 120, the first plate packing 131, the first fixing member 133, the second plate packing 135, the gas detection element 110, a talc ring for use as the sealing filler layer 137, the second fixing member 139, and the crimping ring 141 are inserted in sequence. The crimping portion 120h of the metal shell 120 is crimped in a radially inward direction. The subject crimping forms the sealing filler layer 137 by compression filling the talc ring and retains the gas detection element 110 in the metal shell 120, to thereby obtain the lower assembly 401 shown in FIG. 4.

Meanwhile, the sensor output lead wires 211 and 212 and the heater lead wires 213 are connected to the first and second sensor terminal metal fittings 221 and 222 and the two heater terminal metal fittings 223, and the lead wires 211, 212 and 213 are inserted into the separator 205 in a state where the ceramic heater 115 is positioned inside the first sensor terminal metal fitting 221. The urging member 231 is previously mounted on the separator 205 at a position that is on the periphery and closer to the leading end side than the guard portion 205f.

The separator 205 is inserted into the metal cylinder 200 in a state in which the lead wires 211, 212 and 213 are inserted in the separator 205. After inserting the lead wires 211, 212 and 213 into the lead wire insertion holes formed on the grommet 201, the grommet 201 is fitted into an opening at the base end side of the metal cylinder 200. Thus, the upper assembly 402 shown in FIG. 4 is manufactured.

Figure 4:
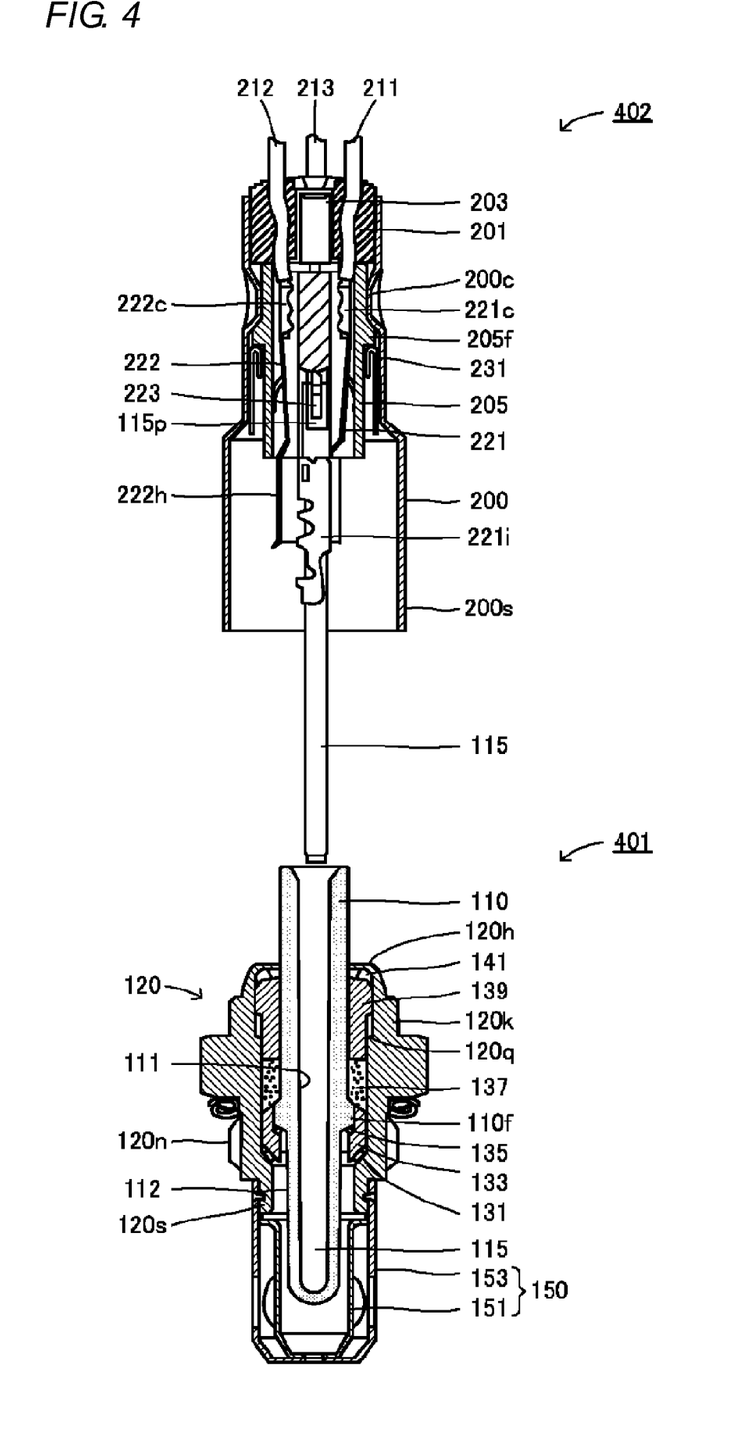
FIG. 4 is a diagram illustrating a method for producing the gas sensor of FIG. 1.

As shown in FIG. 4, the lower assembly 401 and the upper assembly 402 are coaxially disposed, and the upper assembly 402 is moved toward the lower assembly 401 so that the leading end portion 200s of the metal cylinder 200 abuts the base end side of the hexagonal flange portion 120f of the metal shell 120. In this state, the ceramic heater 115 is inserted into the inside of the gas detection element 110. After that, the metal cylinder 200 is pressed toward the leading end side while the leading end portion 200s is crimped by a crimping tool, to thereby temporarily fix the leading end portion 200s of the metal cylinder 200 to the base end portion 120k of the metal shell 120.

Also, the guard portion 205f of the separator 205 is held between the urging member 231 and the inner protruding portion 200c by deforming the urging member 231. This deforming is done by crimping in the radially inward direction a portion of the metal cylinder 200 which is at a position radially outward from the urging member 231, to thereby retain the separator 205 inside the metal cylinder 200. Further, a portion at a position radially outward from the grommet 201 is crimped in the radially inward direction to airtightly fix the grommet 201 to the metal cylinder 200.

After that, the temporarily connected leading end portion 200s of the metal cylinder 200 and the base end portion 120k of the metal shell 120 are subjected to circumferential laser welding. In this manner, the welded portion 300 is formed such that the leading end portion 200s and the base end portion 120k are connected to each other. By fixing the base end portion 12k of the metal shell 120 and the leading end portion 200s of the metal cylinder 200 to each other by way of the welded portion 300, the gas sensor 100 is completed.

EXAMPLES

Hereinafter, the embodiment of the invention will be described in detail with reference to the following examples.

Metal shells 120 having respective chemical compositions in which the Nb contents were varied within a range of 0 to 60 times the content of C in mass % were prepared. Each of the metal shells 120 had a chemical composition of 0.03 mass % of C, 0.2 mass % of Si, 0.3 mass % of Mn, 0.02 mass % of P, 0.003 mass % of S, 16 mass % of Cr, Nb in a content that is 0 to 60 times the content of C in mass %, and Fe and inevitable impurities as a residual portion.

A protector 150 was attached to the metal shell 120, and a gas detection element 110 and the like were assembled to obtain a lower assembly 401 shown in FIG. 4. Meanwhile, a metal cylinder made from SUS304 was prepared as the metal cylinder 200, and a separator 205 and a grommet 201 were assembled to the metal cylinder 200 to obtain an upper assembly 402 shown in FIG. 4.

As shown in FIG. 4, the upper assembly 402 was moved toward the lower assembly 401, and a leading end portion 200s of the metal cylinder 200 was crimped at a portion where a base end 120k of the metal shell 120 and the leading end portion 200s of the metal cylinder 200 overlap to temporarily fix the metal shell 120 and the metal cylinder 200 to each other. Each of the gas sensors 100 (sample Nos. 1 to 11) as shown in FIG. 1 was completed by performing circumferential laser welding on the temporarily fixed portion.

Among the gas sensors 100 of Sample Nos. 1 to 11, the gas sensors 100 of Sample Nos. 4 to 11 in which the Nb content was 2 to 60 times the content of C in mass % correspond to the gas sensor 100 of this invention. Also, the welded portion 300 formed by the laser welding had a size of Wi=0.5 mm and Wj=0.7 mm in a plane identical to an outer diameter surface of the metal shell 120 shown in FIG. 3.

Subsequently, as a salt water spray test, each of the gas sensors 100 thus prepared was retained in an inclined state of 15° to 30° with respect to a vertical line at a temperature of 35±5° C., and salt water in accordance with JIS Z2371 (2007) was sprayed onto the gas sensor 100 for 2250 hours. After that, the presence/absence of corrosion at the welded portion 300 of each of the gas sensors 100 was evaluated. For the evaluation, the gas sensor was completely hermetically sealed, and the gas sensor element 100 was attached to a chamber having a ventilation hole for ventilation of the gas detection element 110. The evaluation was conducted by investigating air leakage between the metal shell 120 and the metal cylinder 200 after pressurizing at a pressure of 0.5 kgf/cm² for 10 minutes inside the chamber. The gas sensor was considered to be subject to corrosion over the entire boundary between the welded portion 300 and the metal shell 120 when air leakage was observed. Also, the evaluation was performed on 10 gas sensors for each of the gas sensors 100 of a specified Nb content/C content. The results are shown in Table 1.

TABLE 1

| Sample No. | Nb Content/ C Content | Number of Gas Sensors in which Corrosion (air leakage) Occurred (among 10 gas sensors) |
|---|---|---|
| 1 | 0 | 5 |
| 2 | 0.5 | 5 |
| 3 | 1 | 2 |
| 4 | 2 | 1 |
| 5 | 3 | 0 |
| 6 | 5 | 0 |
| 7 | 10 | 0 |
| 8 | 20 | 0 |
| 9 | 30 | 0 |
| 10 | 40 | 0 |
| 11 | 60 | 0 |

As is apparent from Table 1, the occurrence of corrosion (air leakage) was detected in two or more of the 10 gas sensors 100 of each of Sample Nos. 1 to 3 obtained using the metal shell 120 in which the Nb content was equal to or less than the content of C in mass %, thereby revealing low corrosion resistance at the welded portion 300. In contrast, the number of gas sensors in which the occurrence of corrosion (air leakage) was detected among the 10 gas sensors 100 of each of Sample Nos. 4 to 11 using the metal shell 120 having an Nb content twice or more that of the content of C in mass % was one or less, which is an accepted level. Also, the occurrence of corrosion (air leakage) was not detected in the gas sensors 100 of Sample Nos. 5 to 11 using the metal shell 120 having an Nb content three times or more that of the content of C in mass %, thereby exhibiting excellent corrosion resistance at the welded portion 300.

While the present invention has been particularly shown and described with reference to exemplary embodiments thereof, it should be understood by those of ordinary skill in the art that various changes in form and detail may be made therein without departing from the spirit and scope of the present invention as defined by the following claims.

This application is based on Japanese Patent Application No. 2008-042562 filed Feb. 25, 2008, the above application incorporated herein by reference in its entirety.

What is claimed is:

1. A gas sensor comprising:
   a gas detection element extending from a leading end thereof to a base end thereof in an axial direction, the leading end of the gas detection element being exposed to a gas to be measured;
   a metal shell extending from a leading end thereof to a base end thereof in the axial direction and holding the gas detection element such that the gas detection element protrudes from the leading end of the metal shell; and
   a metal cylinder extending from a leading end thereof to a base end thereof in the axial direction, a leading end portion of the metal cylinder surrounding a base end portion of the metal shell and being fixed to the metal shell via a circumferential welded portion,
   wherein the metal shell comprises:
   Fe in an amount equal to or more than 50.0 mass %;
   C in an amount of 0.02 mass % to 0.15 mass %;
   Cr in an amount of 11.5 mass % to 18.0 mass %; and
   Nb in an amount equal to or more than twice the amount of C in mass %.

2. The gas sensor according to claim 1, wherein the metal shell further comprises Si, Mn, P and S, where:
   Si is present in an amount of 1.00 mass % or less;
   Mn is present in an amount of 1.25 mass % or less;
   P is present in an amount of 0.06 mass % or less; and
   S is present in an amount of 0.20 mass % or less.

3. The gas sensor according to claim 1, wherein the metal shell comprises: C in an amount of 0.02 mass % to 0.06 mass %, and wherein the metal shell further comprises Si, Mn, P and S, where:

Si is present in an amount of 1.00 mass % or less;

Mn is present in an amount of 1.00 mass % or less;

P is present in an amount of 0.04 mass % or less; and

S is present in an amount of 0.03 mass % or less.

4. The gas sensor according to claim 1, wherein the amount of C contained in the metal cylinder is smaller than that contained in the metal shell in mass %.

5. The gas sensor according to claim 1, wherein the welded portion at an outer surface of the metal shell has a length in the axial direction not less than 0.4 mm but not more than 0.7 mm, as viewed in a section on a plane including an axis of the metal shell.

6. The gas sensor according to claim 1, wherein a maximum depth of the welded portion defined from the outer surface of the metal shell of the welded portion in a radial direction is equal to or less than a half of a thickness of the base end portion of the metal shell in the radial direction.

7. The gas sensor according to claim 1, wherein the amount of Nb contained in a portion of the metal shell in a vicinity of a boundary with the welded portion is smaller than an amount of Nb contained in other portions of the metal shell.

* * * * *